(12) United States Patent
Kishima

(10) Patent No.: US 8,254,641 B2
(45) Date of Patent: Aug. 28, 2012

(54) BIOMETRICS AUTHENTICATION SYSTEM

(75) Inventor: Koichiro Kishima, Kanagawa (JP)

(73) Assignee: Sony Corporation, Tokyo (JP)

( * ) Notice: Subject to any disclaimer, the term of this patent is extended or adjusted under 35 U.S.C. 154(b) by 887 days.

(21) Appl. No.: 12/218,412

(22) Filed: Jul. 15, 2008

(65) Prior Publication Data

US 2009/0028396 A1    Jan. 29, 2009

(30) Foreign Application Priority Data

Jul. 25, 2007    (JP) .................................. 2007-193196

(51) Int. Cl.
*G06K 9/00* (2006.01)
*G06K 9/20* (2006.01)

(52) U.S. Cl. ........ 382/115; 382/124; 382/125; 382/126; 382/127; 382/284

(58) Field of Classification Search .......... 382/124–127, 382/284
See application file for complete search history.

(56) References Cited

U.S. PATENT DOCUMENTS

| | | | |
|---|---|---|---|
| 2002/0183624 A1 | 12/2002 | Rowe et al. | |
| 2006/0142649 A1* | 6/2006 | Sato | 600/310 |
| 2006/0182318 A1* | 8/2006 | Shigeta | 382/124 |
| 2007/0253607 A1* | 11/2007 | Higuchi | 382/124 |
| 2008/0075330 A1* | 3/2008 | Matsumura et al. | 382/115 |
| 2008/0285812 A1* | 11/2008 | Rensen et al. | 382/115 |
| 2009/0036783 A1 | 2/2009 | Kishima | |

FOREIGN PATENT DOCUMENTS

| | | |
|---|---|---|
| JP | 63-047730 A | 2/1988 |
| JP | 10-127609 A | 5/1998 |
| JP | 2000-207535 A | 7/2000 |
| JP | 2000-253203 A | 9/2000 |
| JP | 2002-272744 A | 9/2002 |
| JP | 2004-049705 A | 2/2004 |
| JP | 2004-272821 A | 9/2004 |
| JP | 2005-500095 A | 1/2005 |
| JP | 2005-301552 A | 10/2005 |
| JP | 2007-102729 A | 4/2007 |
| JP | 2007179434 A * | 7/2007 |
| WO | WO 2006/038276 A1 | 4/2006 |

* cited by examiner

*Primary Examiner* — Anand Bhatnagar
*Assistant Examiner* — Soo Park
(74) *Attorney, Agent, or Firm* — Wolf, Greenfield & Sacks, P.C.

(57) ABSTRACT

A biometrics authentication system includes: a detection section; a light source section including a plurality of unit light sources capable of illuminating independently of one another; an image pickup device being arranged on the same side as a side where the light source section is arranged with respect to the detection section; a driving section driving the light source section so that the unit light sources periodically illuminate by time division, and driving the image pickup device so that while an image pickup operation by a first image pickup cell group positioned near each of illuminating unit light sources is suspended, an image pickup operation by a second image pickup cell group positioned farther from each of illuminating unit light sources than the first image pickup cell group is performed; an image processing section; and an authentication section.

19 Claims, 10 Drawing Sheets

BIOMETRICS AUTHENTICATION SYSTEM

CROSS REFERENCES TO RELATED APPLICATIONS

The present invention contains subject matter related to Japanese Patent Application JP 2007-193196 filed in the Japanese Patent Office on Jul. 25, 2007, the entire contents of which being incorporated herein by reference.

BACKGROUND OF THE INVENTION

1. Field of the Invention

The present invention relates to a biometrics authentication system including a light source and an image pickup device.

2. Description of the Related Art

In recent years, the introduction of personal identification techniques (biometrics) using biometrics authentication into access control in a specific area or bank ATMs has begun. As such a method of identifying a living organism, methods using faces, fingerprints, voiceprints, irises, veins and the like as authentication data have been proposed. Among them, the shape pattern of veins under the skin of a finger or a palm hardly changes throughout a lifetime, and is information about the inside of a living organism, so it is difficult to forge, and the method using veins has high safety. Therefore, veins have been used frequently in biometrics authentication.

FIG. 13 shows a schematic view of an example of a biometrics authentication system in a related art proposed in Japanese Unexamined Patent Application Publication No. 2004-272821, Japanese Patent No. 3925338, Japanese Unexamined Patent Application Publication No. 2007-117397 or the like. The biometrics authentication system includes an upper cover 100 on which a light source 101 such as an LED (Light Emitting Diode) is mounted, a cover glass 102, an image pickup lens 104 and an image pickup device 103 such as a CCD (Charge Coupled Device) or a CMOS (Complementary Metal Oxide Semiconductor). In the biometrics authentication system, when a living organism 2 is placed on the cover glass 102, and light passes through the living organism 2 from the top thereof, light is absorbed by blood hemoglobin flowing through veins. Thereby, contrast is changed inside the living organism 2, and a change in contrast is received by the image pickup device 104, thereby vein data of the living organism 2 as image pickup data for biometrics authentication is capable of being obtained.

SUMMARY OF THE INVENTION

In the biometrics authentication system in the related art shown in FIG. 13, the light source 101 and the image pickup device 103 face each other with respect to the cover glass 102 (a detection section where the living organism 2 is placed), thereby reflected light from the surface (skin) of the living organism 2 as a noise component is prevented from entering into the image pickup device 103.

However, for example, in the case where a reduction in the profile of the biometrics authentication system is intended to be achieved for the purpose of mounting the biometrics authentication system on a laptop computer or the like, it is necessary to arrange the light source and the image pickup device on the same side with respect to the cover glass. In the case where the light source and the image pickup device are arranged in such a manner, reflected light from the surface (skin) of the living organism enters into the image pickup device to produce a noise component, and as a result, authentication precision declines.

Thus, in the related art, it is difficult to achieve a balance between a reduction in the profile of the biometrics authentication system and an improvement in authentication precision.

In view of the foregoing, it is desirable to provide a biometrics authentication system capable of achieving a balance between a reduction in the profile of its system configuration and an improvement in authentication precision.

According to an embodiment of the invention, there is provided a biometrics authentication system including: a detection section where a living organism is placed; a light source section including a plurality of unit light sources capable of illuminating independently of one another, the light source section emitting light to the living organism on the detection section; an image pickup device being arranged on the same side as a side where the light source section is arranged with respect to the detection section, the image pickup device obtaining image pickup data of the living organism by a plurality of image pickup cells on the basis of light from the living organism; a driving section driving the light source section and the image pickup device; an image processing section synthesizing a plurality of image pickup data obtained by the image pickup device on the basis of illumination light from each unit light source so as to obtain synthesized image pickup data; and an authentication section performing the authentication of the living organism on the basis of the synthesized image pickup data obtained by the image processing section. In this case, the above-described driving section drives the light source section so that the unit light sources periodically illuminate by time division, and drives the image pickup device so that while an image pickup operation by a first image pickup cell group positioned near each of illuminating unit light sources is suspended, an image pickup operation by a second image pickup cell group positioned farther from each of illuminating unit light sources than the first image pickup cell group is performed.

In the biometrics authentication system according to the embodiment of the invention, when each unit light source in the light source section applies light to a living organism on the detection section, the image pickup data of the living organism on the basis of light from the living organism is obtained by a plurality of image pickup cells in the image pickup device. Then, in the image processing section, synthesized image pickup data is obtained from a plurality of image pickup data on the basis of illumination light from each unit light source, and in the authentication section, the authentication of the living organism on the basis of the synthesized image pickup data is performed. In this case, the unit light sources periodically illuminate by time division, and while the image pickup operation by the first image pickup cell group positioned near each of illuminating unit light sources is suspended, the image pickup operation by the second image pickup cell group positioned farther from each of illuminating unit light sources than the first image pickup cell group is performed, so while light from the inside of the living organism is received by the second image pickup cell group, even if reflected light from the surface of the living organism reaches the first image pickup cell group, the reflected light is not received, so the reception of reflected light from the surface of the living organism which becomes a noise component is prevented. Moreover, the light source section and the image pickup device are arranged on the same side with respect to the detection section, so compared to the case where they face each other with respect to the detection section, the thickness of the whole system is reduced.

In the biometrics authentication system according to the embodiment of the invention, the unit light sources periodically illuminate by time division, and while the image pickup operation by the first image pickup cell group positioned near each of illuminating unit light sources is suspended, the image pickup operation by the second image pickup cell group positioned farther from each of illuminating unit light sources than the first image pickup cell group is performed, so the reception of reflected light from the surface of the living organism which becomes a noise component is able to be prevented. Moreover, the light source section and the image pickup device are arranged on the same side with respect to the detection section, so compared to the case where they face each other with respect to the detection section, the thickness of the whole system is able to be reduced. Therefore, it becomes possible to achieve a balance between a reduction in the profile of the system and an improvement in authentication precision.

Other and further objects, features and advantages of the invention will appear more fully from the following description.

DETAILED DESCRIPTION OF THE PREFERRED EMBODIMENTS

A preferred embodiment will be described in detail below referring to the accompanying drawings.

Figure 1:
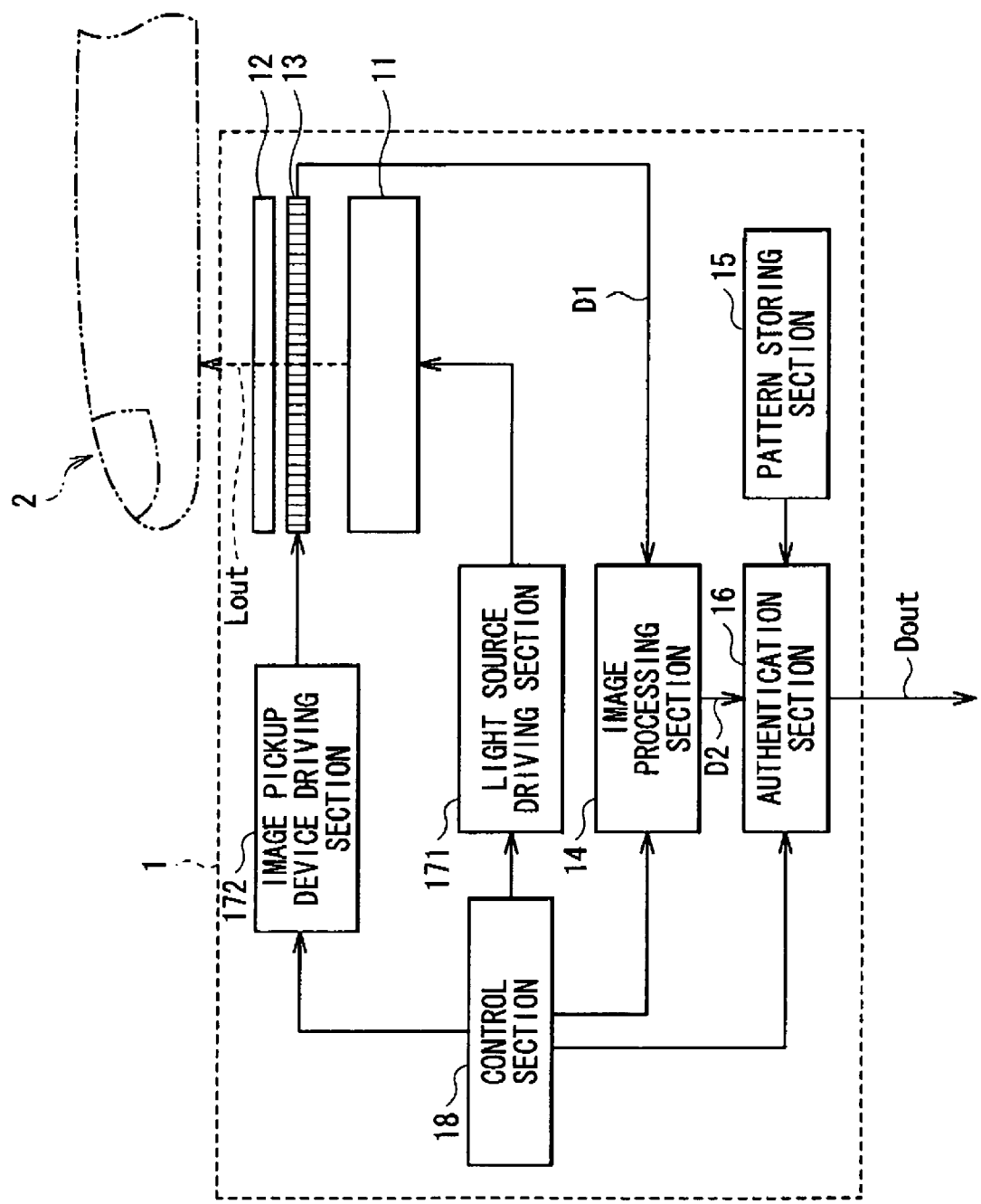
FIG. 1 is a functional block diagram showing a biometrics authentication system according to an embodiment of the invention.
Figure 2:
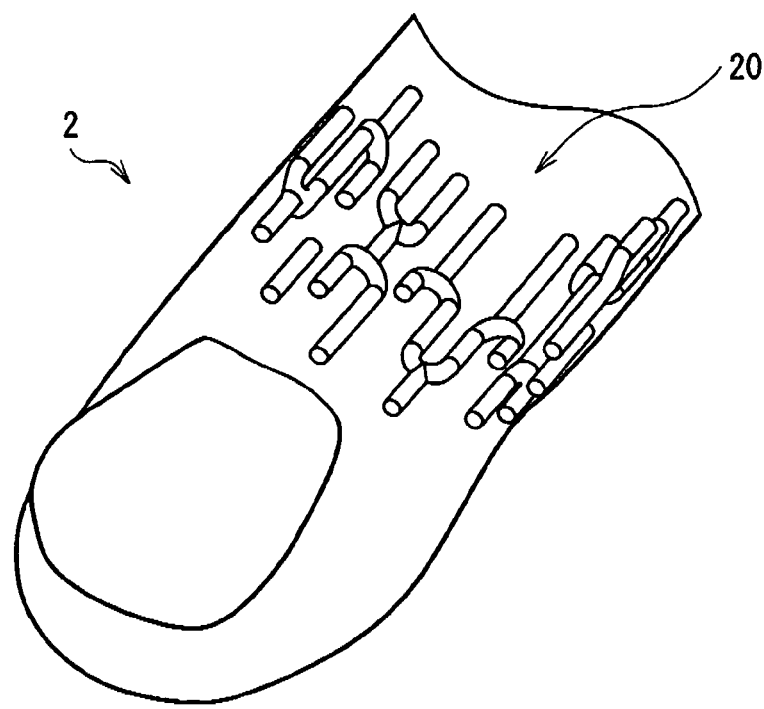
FIG. 2 is schematic perspective view showing a living organism (fingertip) and the form of veins in the living organism.

FIG. 1 shows a functional block diagram of a biometrics authentication system (a biometrics authentication system 1) according to an embodiment of the invention. The biometrics authentication system 1 picks up an image of a living organism (for example, a living organism (fingertip) 2 shown in FIG. 2) to perform biometrics authentication (for example, in the case shown in FIG. 2, the biometrics authentication system 1 picks up an image of veins 20 inside the living organism 2 to perform vein authentication), and then outputs an authentication result (authentication result data Dout which will be described later), and the biometrics authentication system 1 includes a light source section 11, a cover glass 12, an image pickup device 13, an image processing section 14, a pattern storing section 15, an authentication section 16, a light source driving section 171, an image pickup device driving section 172 and a control section 18.

The light source section 11 applies light to the living organism 2 as an object subjected to image pickup on the cover glass 12 from the bottom of the living organism 2, and is made of, for example, an LED (Light Emitting Diode) or the like. The light source section 11 includes a plurality of unit light sources (unit light sources 110 which will be described later) capable of illuminating independently of one another. The light source section 11 preferably emits light of a near-infrared wavelength region (a wavelength region approximately from 700 nm to 1200 nm). It is because in the case where light of such a wavelength region is used, by a balance between the transmittance through a living organism 2 and the absorption by reduced hemoglobin (veins) in the living organism 2, light use efficiency at the time of the vein authentication of the living organism 2 is able to be further improved. The specific configuration of the light source section 11 will be described later.

The cover glass 12 is arranged on the image pickup device 13, and is a section protecting the interior of the biometrics authentication system 1. The surface of the cover glass 12 is a section where the living organism 2 is placed during authentication (a detection section).

The image pickup device 13 is arranged on the same side as a side where the light source section 11 is arranged with respect to the cover glass 12, and receives light from the living organism 2 through the use of a plurality of image pickup cells (image pickup cells 130 which will be described later) to obtain image pickup data D1 of the living organism 2. The image pickup device 13 includes CCDs or the like arranged in a matrix form. The specific configuration of the image pickup device 13 will be described later.

The image processing section 14 performs predetermined image processing on the image pickup data D1 obtained by the image pickup device 13 to obtain image-processed data, and outputs the image-processed data to the authentication section 16. More specifically, the image processing section 14 synthesizes a plurality of image pickup data D1 obtained by the image pickup device 13 on the basis of light applied from the unit light sources in the light source section 11 to obtain synthesized image pickup data D2 corresponding to one picked-up image, and then outputs the image pickup data D2 to the authentication section 16. In addition, the image processing section 14, and the authentication section 16 and the control section 18 which will be described later each include, for example, a microcomputer or the like.

The pattern storing section 15 is a section storing a biometrics authentication pattern (which is a comparison pattern relative to an image pickup pattern obtained at the time of authentication, and which is obtained by picking up an image of a living organism in advance), and includes a nonvolatile memory device (for example, an EEPROM (Electrically Erasable Programmable Read Only Memory) or the like).

The authentication section 16 is a section performing the authentication of the living organism 2 as an object subjected to image pickup by comparing an image pickup pattern (an image pickup pattern of the synthesized image pickup data D2) outputted from the image processing section 14 to the biometrics authentication pattern stored in the pattern storing section 15 in response to the control of the control section 18.

The light source driving section 171 drives the light source section 11 to emit light in response to the control of the control section 18. More specifically, although detailed description will be given later, the light source driving section 171 drives the light source section 11 so that each unit light source in the light source section 11 periodically illuminates by time division. On the other hand, the image pickup device driving section 172 drives the image pickup device 13 to pick up an image (to receive light) in response to the control of the control section 18. More specifically, although detailed description will be given later, the image pickup device driving section 172 drives the image pickup device 13 so that while an image pickup operation by an image pickup cell group (a first image pickup cell group) positioned near each of illuminating unit light sources is suspended, an image pickup operation by an image pickup cell group (a second image pickup cell group; an image pickup cell group in an image pickup region 13A which will be described later) positioned farther from each of illuminating unit light sources than the above-described first image pickup cell group is performed. Moreover, although detailed description will be described later, the light source driving section 171 and the image pickup device driving section 172 drive the light source section 11 and the image pickup device 13, respectively, so that the unit light sources in the light source section 11 and the above-described first and second image pickup cell groups synchronize with each other to perform a periodical line-sequential operation in response to the control of the control section 18.

The control section 18 controls the operations of the image processing section 14, the authentication section 16, the light source driving section 171 and the image pickup device driving section 172.

Figure 3:
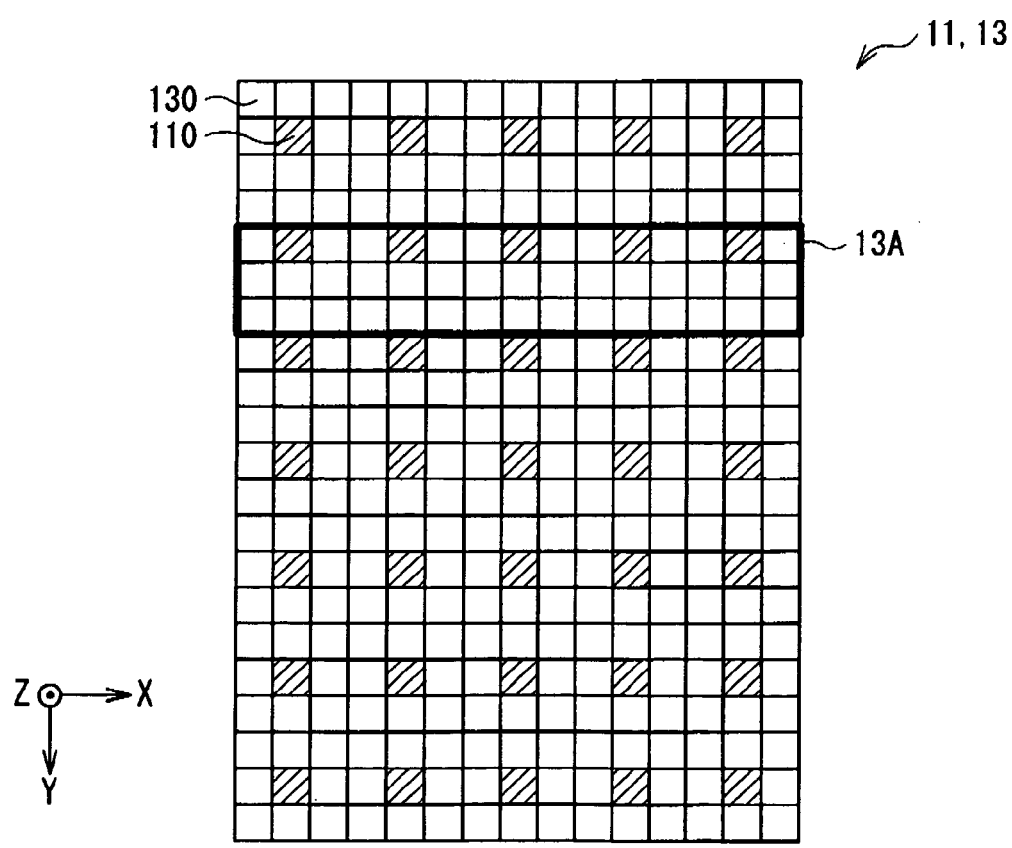
FIG. 3 is a plan view showing specific configuration examples of a light source section and an image pickup device shown in FIG. 1.

Next, referring to FIGS. 3 to 6A and 6B, the specific configurations of the light source section 11, the image pickup device 13 and the like will be described below. FIG. 3 shows a plan view (an X-Y plan view) of specific configuration examples of the light source section 11 and the image pickup device 13, and FIG. 4 shows a sectional view (a Y-Z sectional view) of a specific configuration example of a main part of the biometrics authentication system 1.

As shown in FIG. 3, in the light source section 11 and the image pickup device 13, unit light sources 110 (illumination cells) and the image pickup cells 130 each are arranged in a matrix form, and the unit light sources 110 are arranged in gaps between the image pickup cells 130. In other words, in the image pickup region 13A which will be described in detail later, the number of the image pickup cells 130 is preferably larger than the number of unit light sources 110. Moreover, to prevent variations in illumination by the unit light sources 110, in one image pickup region 13A, a plurality of unit light sources 110 are preferably arranged (in FIG. 3, 5 unit light sources 110 are arranged). In other words, the above-described light source driving section 171 preferably drives the light source section 11 so that a plurality of unit light sources 110 illuminate at the time of an image pickup operation by the image pickup region 13A. In addition, the image pickup region 13A is preferably set to be a region where the intensity of illumination light from each of the unit light sources 110 is uniform to some extent.

Figure 4:
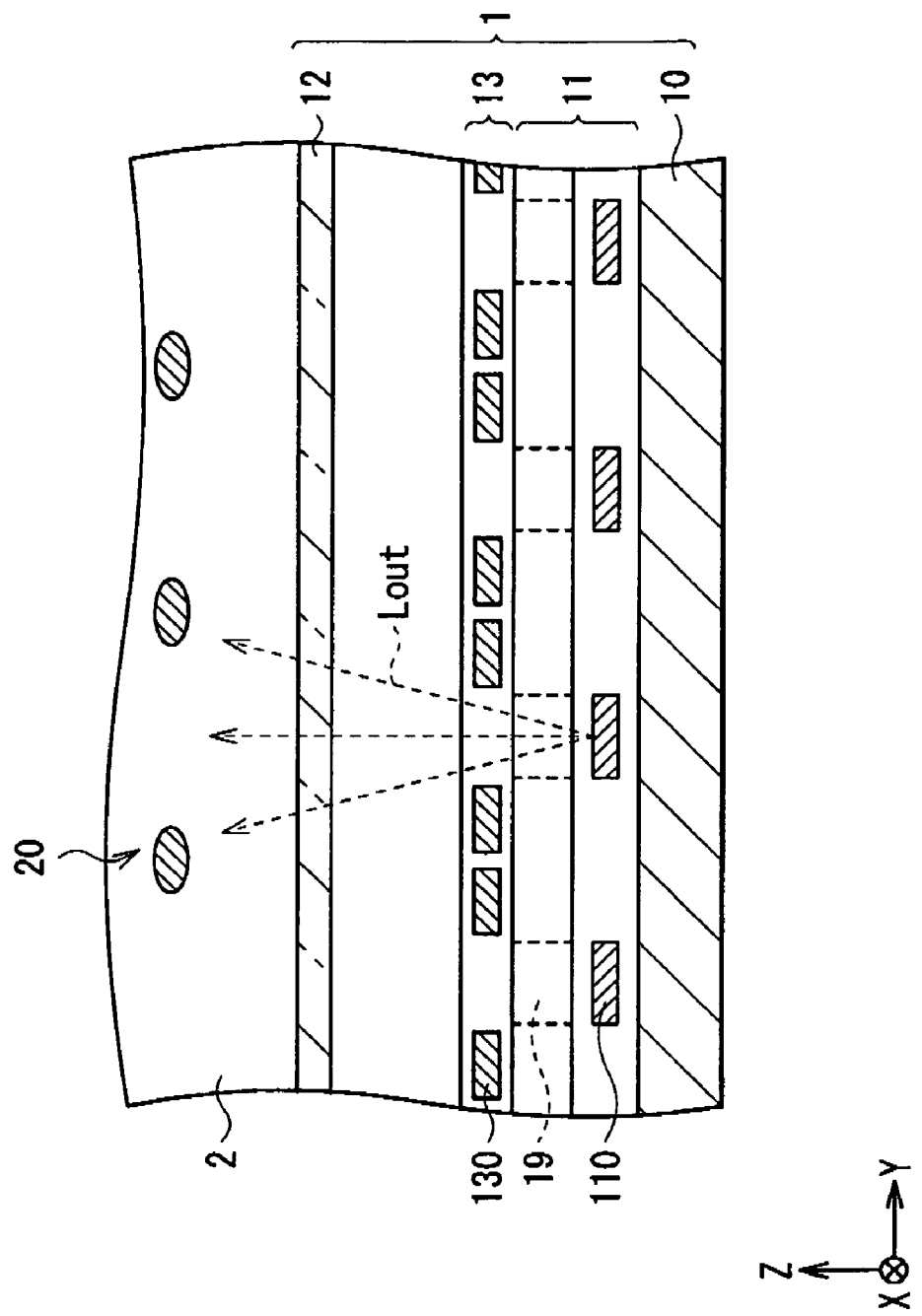
FIG. 4 is a sectional view showing a specific configuration example of a main part of the biometrics authentication system shown in FIG. 1.

Moreover, as shown in FIG. 4, in the biometrics authentication system 1, the light source section 11 including a plurality of unit light sources 110, the image pickup device 13 including a plurality of image pickup cells 130 and the cover glass 12 are laminated in this order on a substrate 10. When the living organism 2 is placed on the cover glass 12, each unit light source 110 applies light (illumination light) Lout to veins 20 in the living organism 2. Moreover, in the light source section 11, in addition to such unit light sources 110, a switching section 19 which is selectively switchable between transmission and blocking of light Lout in response to the application of a voltage from the light source driving section 171 is arranged on each unit light source 110.

Figure 5:
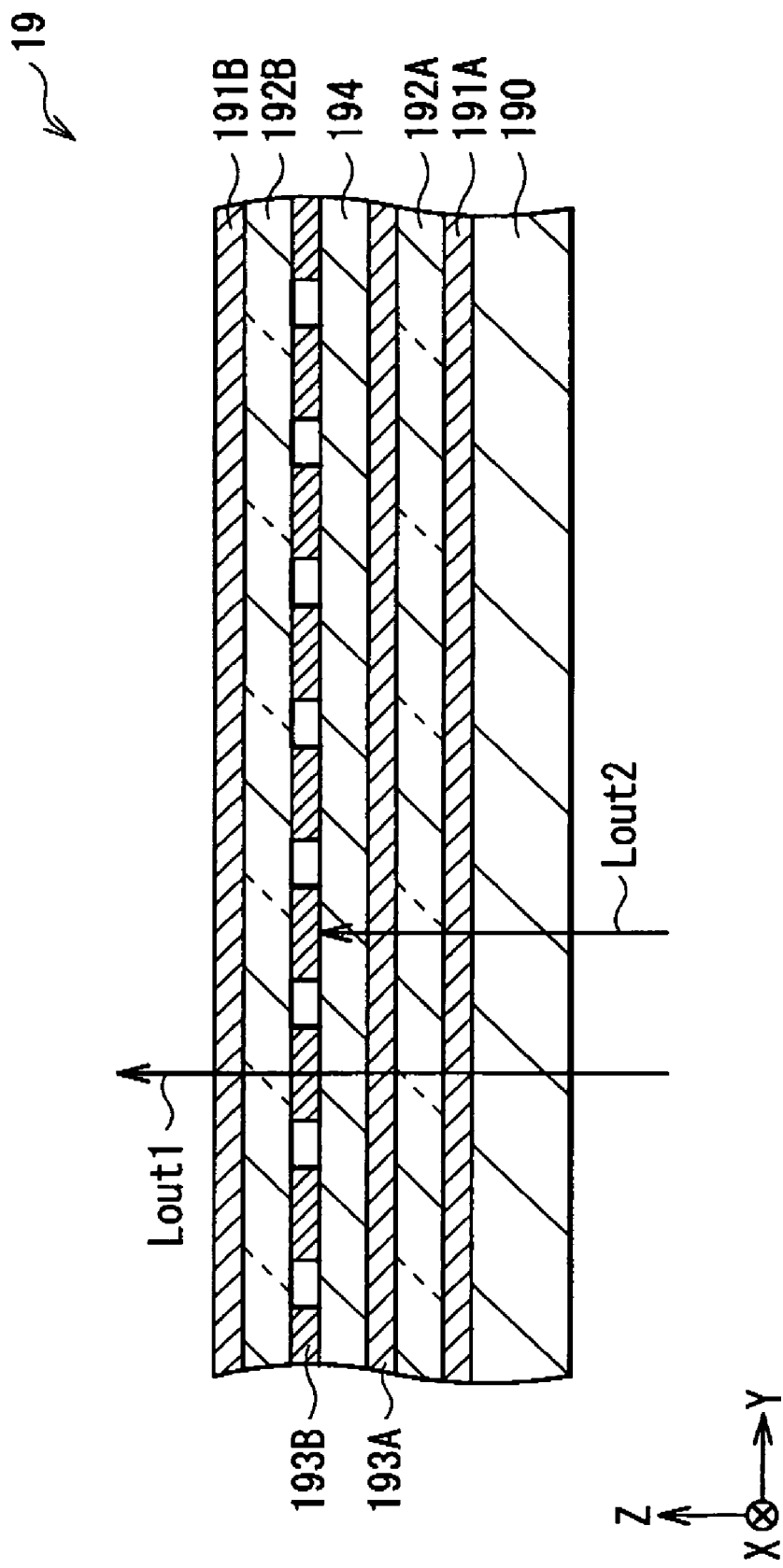
FIG. 5 is a sectional view showing a specific configuration example of a switching section shown in FIG. 4.
Figure 6A:
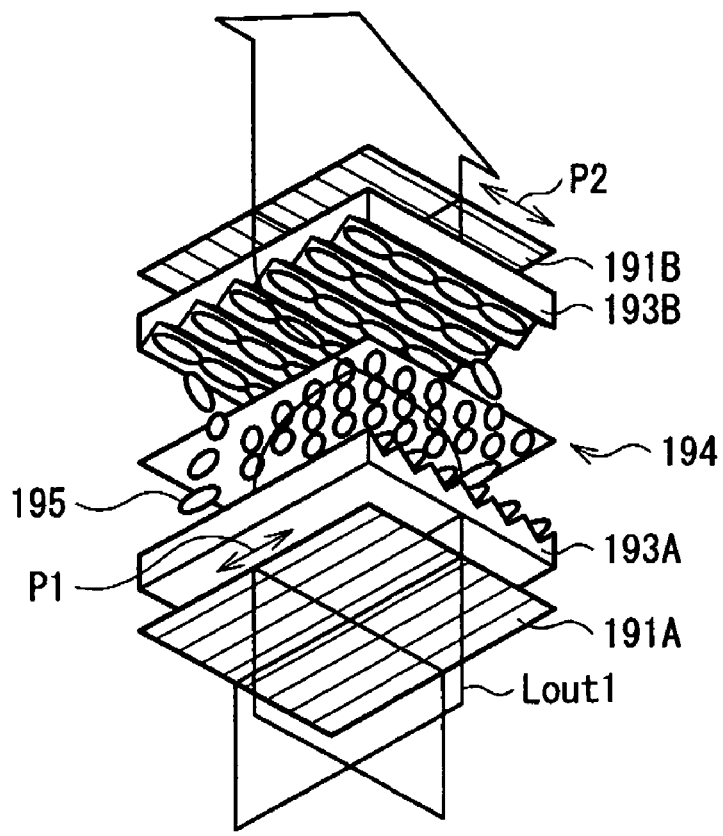
FIGS. 6A and 6B are perspective views for describing a function of the switching section shown in FIG. 5.
Figure 6B:
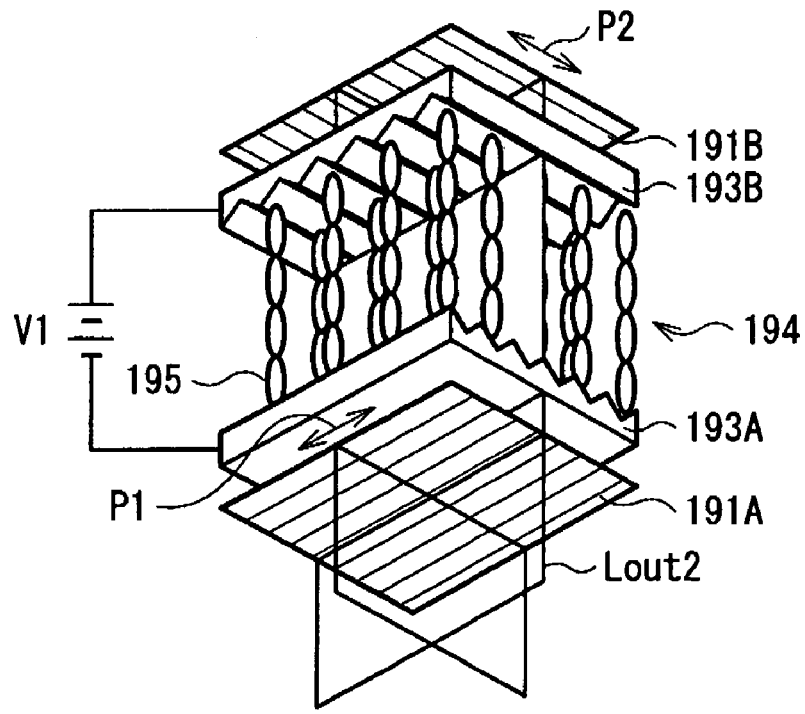

The switching section 19 includes a liquid crystal device shown in, for example, a sectional view (a Y-Z sectional view) in FIG. 5. More specifically, the switching section 19 has a laminate configuration in which a light guide plate 190, a polarizing plate 191A, a glass substrate 192A, a transparent electrode 193A, a liquid crystal layer 194, a transparent electrode 193B, a glass substrate 192B and a polarizing plate 191B are laminated in this order. The polarizing axes of polarizing plates 191A and 191B are orthogonal to each other (refer to arrows P1 and P2 shown in FIGS. 6A and 6B). Moreover, the transparent electrode 193A is a common electrode for the unit light sources 110, and the transparent electrode 193B is an independent electrode for each unit light source 110. In the switching section 19 with such a configuration, for example, as shown in FIG. 6A, in the case where a voltage is not applied between the transparent electrodes 193A and 193B, the orientation directions of liquid crystal molecules 195 in the liquid crystal layer 194 are twisted, so light (illumination light Lout1) from the unit light sources 110 passes through the switching section 19 via the polarizing plate 191B, and for example, as shown in FIG. 6B, in the case where a predetermined voltage V1 is applied between the transparent electrodes 193A and 193B, the orientation directions of liquid crystal molecules 195 in the liquid crystal layer 194 are aligned in a vertical direction, so light (illumination light Lout2) from the unit light sources 110 does not pass through the polarizing plate 191B, and is blocked by the switching section 19. Thus, when the application of a voltage to the switching section 19 is controlled by the light source driving section 171, each unit light source 110 is capable of illuminating independently (that is, light Lout from each unit light source 110 independently passes through or is blocked).

Figure 7:
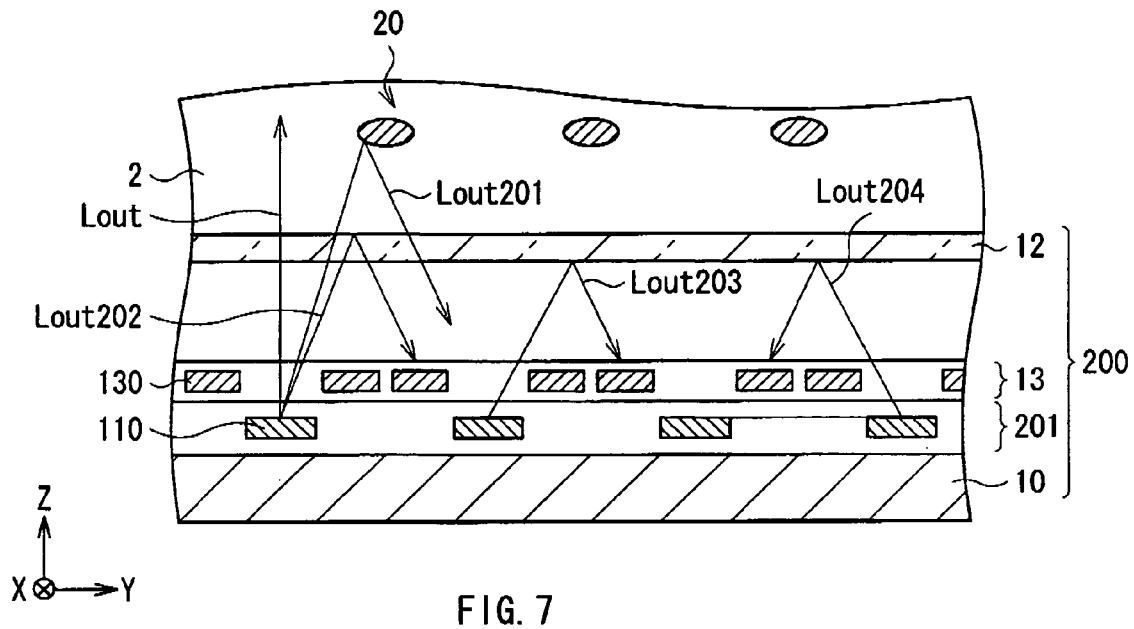
FIG. 7 is a sectional view for describing an image pickup operation in a biometrics authentication system according to a comparative example.
Figure 8:
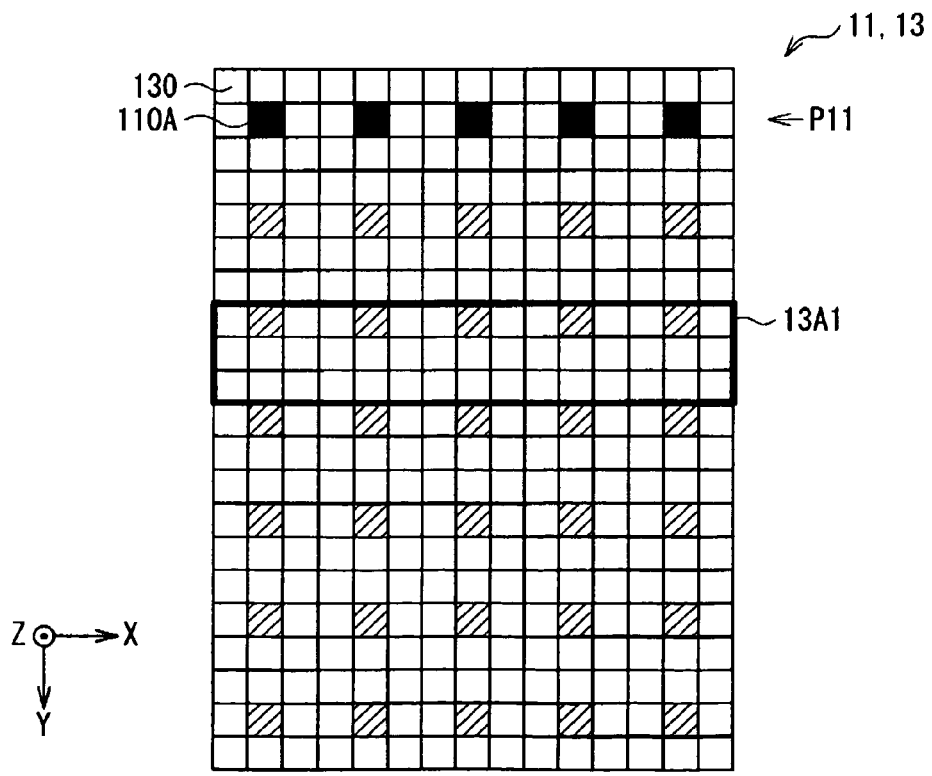
FIG. 8 is a plan view for describing a line-sequential image pickup operation in the biometrics authentication system according to the embodiment of the invention.
Figure 9:
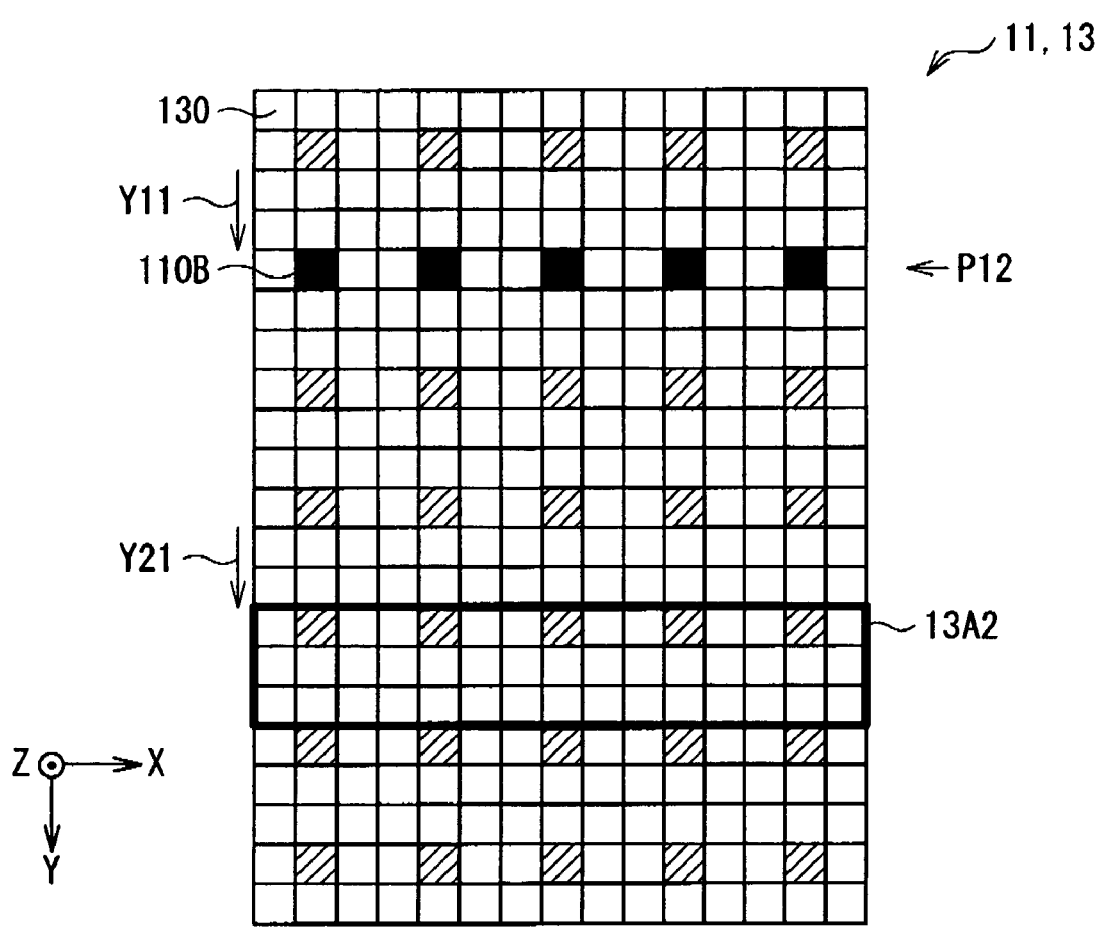
FIG. 9 is a plan view for describing a line-sequential image pickup operation following FIG. 8.
Figure 10:
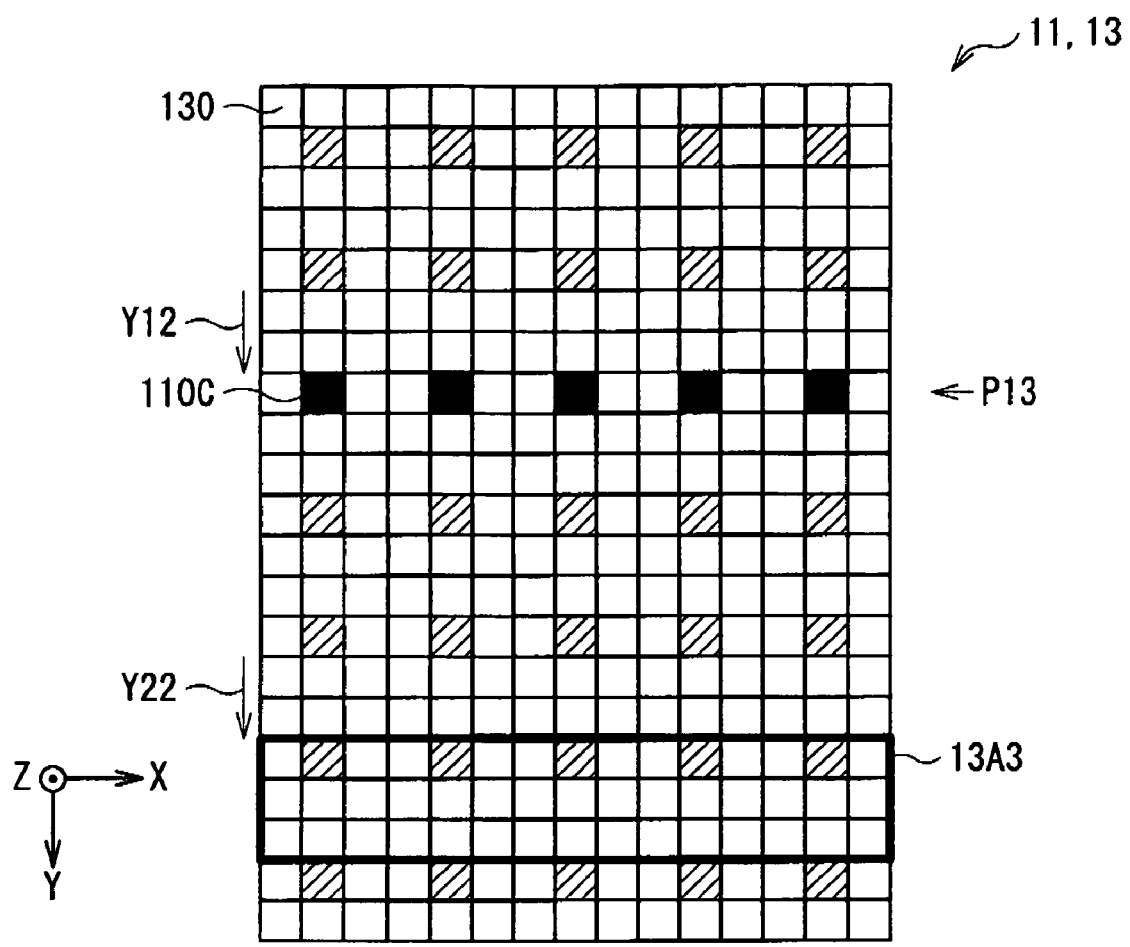
FIG. 10 is a plan view for describing a line-sequential image pickup operation following FIG. 9.
Figure 11:
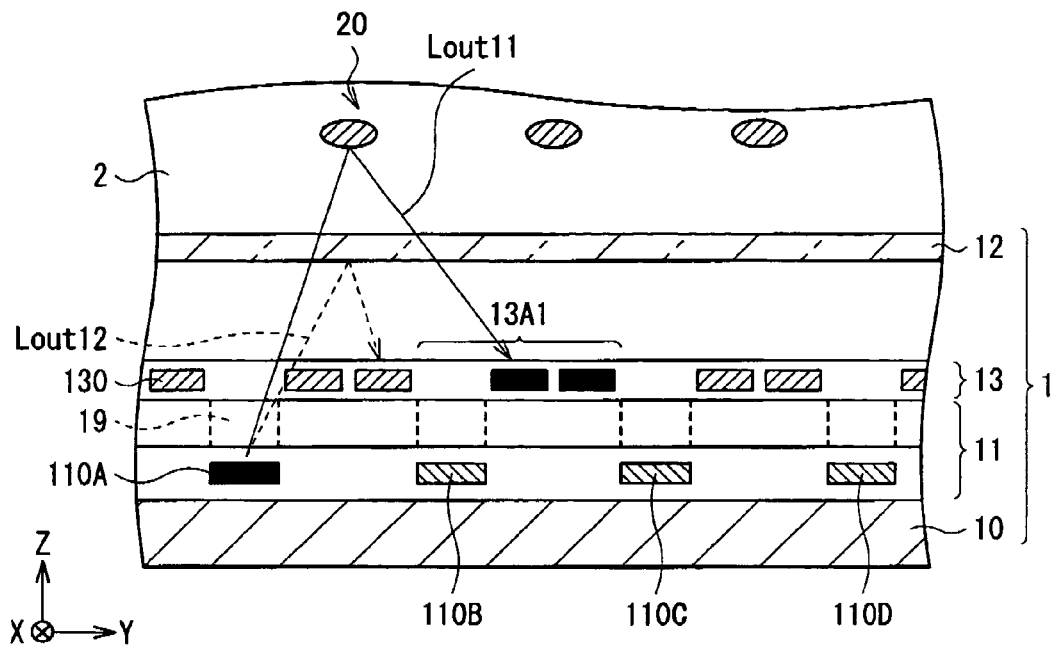
FIG. 11 is a sectional view for describing the line-sequential image pickup operation shown in FIG. 8.
Figure 12:
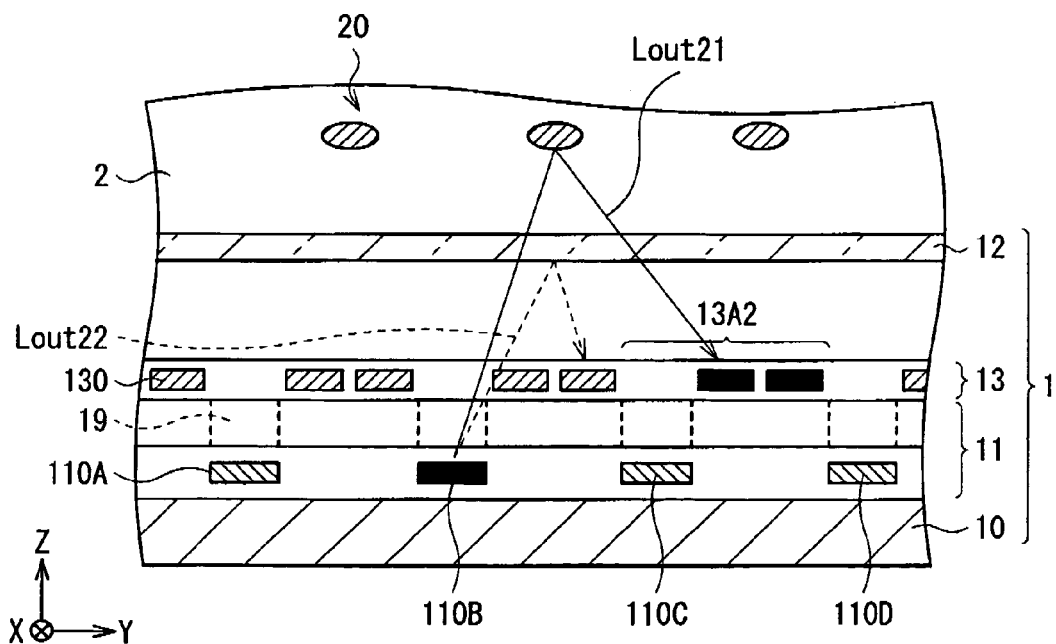
FIG. 12 is a sectional view for describing the line-sequential image pickup operation shown in FIG. 9.
Figure 13:
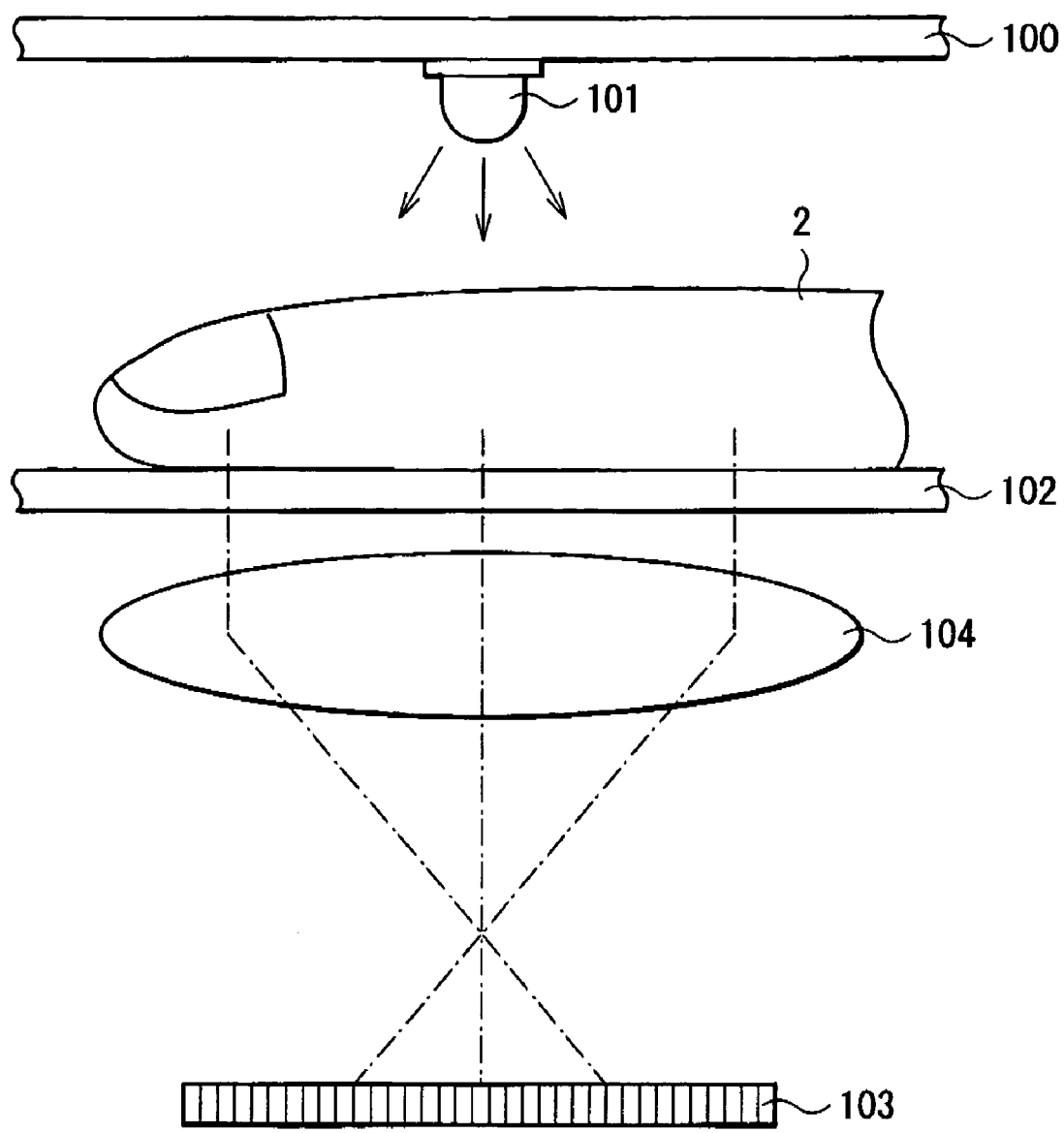
FIG. 13 is a sectional view showing an example of a main part of a biometrics authentication system in a related art.

Next, referring to FIGS. 1 to 12, the operation (a biometrics authentication process) of the biometrics authentication system 1 will be described in detail as compared to a comparative example. FIG. 7 shows a sectional view (a Y-Z sectional view) and the operation of a biometrics authentication system (a biometrics authentication system 101) according to the comparative example. FIGS. 8 to 10 are plan views (X-Y plan views) showing the operation of the biometrics authentication system 1 according to the embodiment, and FIGS. 11 and 12 are sectional views (Y-Z sectional views) showing the operation of the biometrics authentication system 1.

In the biometrics authentication system 1, for example, as shown in FIG. 1, when the living organism (for example, a fingertip) 2 is placed on the cover glass 12, light Lout is emitted from the light source section 11 by the diving operation of the light source driving section 171, and is applied to the living organism 2 via the image pickup device 13 and the cover glass 12. When an image of the living organism 2 is picked up in this state, light from the living organism 2 is condensed on each image pickup cell 130 of the image pickup device 13, thereby image pickup data D1 (a vein pattern) of veins of the living organism 2 is obtained. The image pickup data D1 obtained by the image pickup device 13 in such a manner is subjected to image processing (an image synthesizing process) in the image processing section 14, and is supplied to the authentication section 16 as synthesized image pickup data D2 corresponding to one picked-up image.

In the authentication section 16, the synthesized image pickup data D2 (the vein pattern) which is inputted into the authentication section 16 is compared to an authentication pattern for vein authentication stored in the pattern storing section 15, thereby vein authentication is performed. Then, in the authentication section 16, a final biometrics authentication result (authentication result data Dout) is outputted, thereby a biometrics authentication process is completed.

In the case where an image of light from the living organism 2 on the basis of the illumination light Lout from each unit light source 110 is picked up (the light is received) by the image pickup device 13, for example, as in the case of a biometrics authentication system 200 (the comparative example) shown in FIG. 7, in addition to light Lout201 from veins 20 in the living organism 2, reflected light Lout202, Lout203, Lout204 or the like from the surface (skin) of the living organism 2 enters into each image pickup cell 130 in the image pickup device 13. Therefore, in the biometrics authentication system 200 according to the comparative example, such reflected light from the surface of the living organism 2 is also received by the image pickup device 13 to cause a noise component, and as a result, the authentication precision of the living organism 2 declines.

In the biometrics authentication system 1 according to the embodiment, by the driving operations of the light source driving section 171 and the image pickup device 172, each unit light source 110 periodically illuminates by time division, and while the image pickup operation by the image pickup cell group (the first image pickup cell group) positioned near each of illuminating unit light sources 110 is suspended, the image pickup operation by the image pickup cell group (the second image pickup cell group) positioned farther from each of illuminating unit light sources 110 than the first image pickup cell group is performed.

More specifically, for example, as shown in FIGS. 8 to 10, the light source section 11 and the image pickup device 13 are driven so that the unit light sources 110 and the first and second image pickup cell groups (the image pickup region 13A) synchronize with each other to perform a periodical line-sequential operation. For example, a state in which the unit light sources 110A on a line indicated by an arrow P11 in FIG. 8 and an image pickup region 13A1 as an image pickup region by the second image pickup cell group synchronize with each other is changed to a state in which unit light sources 110B on a line indicated by the arrow P12 in FIG. 9 and an image pickup region 13A2 as an image pickup region by the second image pickup cell group synchronize with each other (refer to arrows Y11 and Y21 in FIG. 9). Then, the state in which the unit light sources 110B and the image pickup region 13A2 synchronize with each other is changed to a state in which unit light sources 110C on a line indicated by an arrow P13 in FIG. 10 and an image pickup region 13A3 as an image pickup region by the second image pickup cell group synchronize with each other (refer to arrows Y12 and Y22 in FIG. 10).

Therefore, for example, as shown in FIGS. 11 and 12, while light Lout11 or Lout21 from the inside (the veins 20) of the living organism 2 on the basis of illumination light from an illuminating unit light source 110A or 110B is received by the image pickup region 13A1 or 13A2 corresponding to the second image pickup cell group, even if reflected light Lout12 or Lout22 from the surface of the living organism 2 reaches the image pickup cells 130 (the first image pickup cell group) positioned nearer the unit light source 110A or 110B than the image pickup region 13A1 or 13A2, the reflected light Lout12 or Lout22 is not received by the image pickup device 13, because the first image pickup cell group does not become an image pickup region (the image pickup operation is suspended). Therefore, the reflected light Lout12 or Lout22 from the surface of the living organism 2 is not received by the first image pickup cell group, thereby the reception of reflected light from the surface of the living organism 2 which becomes a noise component is prevented.

As described above, in the embodiment, each unit light source 110 in the light source section 11 periodically illuminates by time division, and while the image pickup operation by the image pickup cell group (the first image pickup cell group) positioned near each of illuminating unit light sources 110 is suspended, the image pickup operation by the image pickup cell group (the second image pickup cell group) positioned farther from each of illuminating unit light sources 110 than the first image pickup cell group is performed, so the reception of reflected light from the surface of the living organism 2 which becomes a noise component is able to be prevented. Moreover, the light source section 11 and the image pickup device 13 are arranged on the same side with respect to the cover glass 12 (a detection section), so compared to the case where they face each other with respect to the cover glass 12, the thickness of the whole system is able to be reduced. Therefore, it becomes possible to achieve a balance between a reduction in the profile of the system and an improvement in authentication precision.

Further, the unit light sources 110 and the image pickup cells 130 are arranged in a matrix form in the light source section 11 and the image pickup device 13, respectively, and the unit light sources 110 and the above-described first and second image pickup cell groups synchronize each other to perform a periodical line-sequential operation, so by a simple driving operation, the reception of reflected light from the surface of the living organism 2 which becomes a noise component as described above is able to be prevented.

Although the present invention is described referring to the embodiment, the invention is not limited to the embodiment, and may be variously modified.

For example, in the above-described embodiment, the case where the unit light sources 110 and the above-described first and second image pickup cell groups synchronize with each other to perform a periodical line-sequential operation is described; however, the reception of reflected light from the surface of the living organism 2 which becomes a noise component may be prevented by any other driving operation.

Moreover, in the above-described embodiment, the case where the switching section 19 includes the liquid crystal device which is selectively switchable between transmission and blocking of light according to the application of a voltage is described; however, for example, a large number of LED chips arranged may emit light directly and selectively so that each unit light source 110 illuminates independently.

Further, in the above-described embodiment, the biometrics authentication system (a vein authentication system) performing the authentication of a living organism on the basis of image pickup data of veins as an object subjected to image pickup is described; however, the invention is applicable to, for example, any other biometrics authentication system performing the authentication of a living organism on the basis of image pickup data of any other part of the living organism 2 as an object subjected to image pickup.

It should be understood by those skilled in the art that various modifications, combinations, sub-combinations and alterations may occur depending on design requirements and other factors insofar as they are within the scope of the appended claims or the equivalents thereof.

What is claimed is:

1. A biometrics authentication system comprising:
a detection section where a living organism is placed;
a light source section including a plurality of laterally-spaced unit light sources capable of illuminating independently of one another, the light source section adapted to illuminate the living organism on the detection section;
an image pickup device arranged on a same side as a side where the light source section is arranged with respect to the detection section, the image pickup device adapted to obtain image pickup data of the living organism by a plurality of laterally-spaced image pickup cells on a basis of light from the living organism;
a driving section to drive the light source section so that the unit light sources periodically illuminate by time division, and to drive the image pickup device so that while an image pickup operation by a first image pickup cell group laterally positioned near each of the illuminating unit light sources is suspended, an image pickup operation by a second image pickup cell group laterally positioned farther from each of the illuminating unit light sources than the first image pickup cell group is performed;
an image processing section to synthesize a plurality of image pickup data obtained by the image pickup device on a basis of illumination light from each unit light source so as to obtain synthesized data representative of an image; and
an authentication section to perform an authentication of the living organism on a basis of the synthesized image pickup data obtained by the image processing section.

2. The biometrics authentication system according to claim 1, wherein
the unit light sources and the image pickup cells each are arranged in a matrix form, and
the driving section drives the light source section and the image pickup device so that the unit light sources and the first and second image pickup cell groups synchronize with each other to perform a periodical line-sequential operation.

3. The biometrics authentication system according to claim 1, wherein
the light source section includes a liquid crystal device which is selectively switchable between transmission and blocking of light according to application of a voltage, and
the driving section controls the application of the voltage to the liquid crystal device, thereby each unit light source illuminates independently.

4. The biometrics authentication system according to claim 1, wherein
the driving section drives the light source section so that a plurality of unit light sources illuminate at the time of each image pickup operation by the second image pickup cell group.

5. The biometrics authentication system according to claim 1, wherein the plurality of unit light sources are light sources emitting light of a near-infrared wavelength region.

6. The biometrics authentication system according to claim 1, wherein
the image pickup data is image pickup data of veins of the living organism as an object subjected to image pickup, and
the authentication section performs the authentication of the living organism on the basis of the image pickup data of veins as an object subjected to image pickup.

7. A biometrics authentication system comprising:
a detection section for receiving an organism, the detection section arranged on a first side of the authentication system;
a light source section arranged on the first side and having a plurality of laterally-spaced unit light sources that are configured to operate independently of each other to illuminate a region of the detection section that receives the organism;
an image pick-up device arranged on the first side and configured to obtain image pick-up data of the organism by a plurality of laterally-spaced image pick-up cells responsive to illumination of the organism by the light sources; and
a driving section configured to drive the light source section so that selected unit light sources periodically illuminate by time division, and to drive the image pickup device so that a first group of image pick-up cells laterally positioned near selected illuminating light sources are suspended and a second group of image pick-up cells laterally positioned farther from the selected illuminating light sources acquire image pick-up data representative of an image.

8. The system of claim 7, further comprising:
an image processing section configured to synthesize a plurality of image pick-up data obtained by the image pickup device to produce synthesized image pickup data; and
an authentication section to perform an authentication of the organism based on the synthesized image pickup data.

9. The system of claim 7, wherein the laterally-spaced unit light sources and laterally-spaced image pick-up cells are disposed in an interleaved two-dimensional matrix.

10. The system of claim 7, wherein the second group of image pick-up cells is laterally located to receive significantly less light from the unit light sources that is reflected from a surface of the organism than the first group of image pick-up cells.

11. The system of claim 7, wherein the unit light sources are configured to emit near-infrared radiation.

12. The system of claim 7, wherein the image pick-up data is representative of a vein pattern within the organism.

13. A method of biometric authentication comprising:
illuminating an area on a first side of a biometric authentication device on which an organism may be placed by a light source section arranged on the first side and having a plurality of laterally-spaced unit light sources;
obtaining, by an image pick-up device arranged on the first side, image pick-up data of the organism by a plurality of laterally-spaced image pick-up cells of the image pick-up device responsive to the illuminating of the organism;
driving, by a driving section, selected unit light sources of the light source section to periodically illuminate, by time division, the organism; and
driving, by the driving section, the image pickup device so that a first group of image pick-up cells laterally positioned near selected illuminating light sources do not acquire image pick-up data and a second group of image pick-up cells laterally positioned farther from the selected illuminating light sources acquire image pick-up data representative of an image responsive to the selected illuminating light sources.

14. The method of claim 13, further comprising processing the image pick-up data to produce image data representative of vein patterns within the organism.

15. The method of claim 14, further comprising performing, by an authentication section, an authentication of the organism based upon the produced image data.

16. The method of claim 13, wherein the laterally-spaced unit light sources and laterally-spaced image pick-up cells are disposed in an interleaved two-dimensional matrix.

17. The method of claim 16, wherein the acts of driving each comprise driving the selected unit light sources, the first group of image pick-up cells, and the second group of image pick-up cells in a synchronized line-sequential manner.

18. The method of claim 17, wherein the second group of image pick-up cells is disposed in a line positioned farther from the selected unit light sources than the first group of image pick-up cells.

19. The method of claim 13, wherein the illuminating comprises illuminating the area on a first side of a biometric authentication device with near-infrared radiation.

* * * * *